United States Patent [19]

D'Amico

[11] E Patent Number: Re. 32,769

[45] Reissued Date of Patent: Oct. 18, 1988

[54] AMIDES AND HYDRAZIDES OF 2-OXO-BENZOTHIAZOLINE-3-ACETIC ACID

[75] Inventor: John J. D'Amico, St. Louis, Mo.

[73] Assignee: Monsanto Company, St. Louis, Mo.

[21] Appl. No.: 88,211

[22] Filed: Oct. 24, 1979

Related U.S. Patent Documents

Reissue of:

[64] Patent No.: 4,075,216
Issued: Feb. 21, 1978
Appl. No.: 735,658
Filed: Oct. 26, 1976

[51] Int. Cl.[4] ..... C07D 413/12; C07D 263/58

[52] U.S. Cl. ..... 546/280; 548/170; 548/171; 71/91; 71/90; 71/88

[58] Field of Search ..... 548/170, 171; 546/280

[56] References Cited

U.S. PATENT DOCUMENTS

| | | | |
|---|---|---|---|
| 2,412,510 | 12/1946 | Jones | 71/98 |
| 2,577,969 | 12/1951 | Jones | 71/98 |
| 2,782,111 | 2/1957 | Bloch | 71/98 |
| 3,661,921 | 5/1972 | D'Amico | 260/304 B |
| 3,993,468 | 11/1976 | D'Amico | 71/90 |
| 4,049,419 | 9/1977 | D'Amico | 71/90 |
| 4,075,216 | 2/1978 | D'Amico | 71/90 |

FOREIGN PATENT DOCUMENTS

| | | | |
|---|---|---|---|
| 42-1669 | 1/1967 | Japan . | |
| 862226 | 3/1961 | United Kingdom | 71/2.5 |

*Primary Examiner*—Richard L. Raymond
*Assistant Examiner*—D. B. Springs
*Attorney, Agent, or Firm*—J. Timothy Keane; Howard C. Stanley; Arnold H. Cole

[57] ABSTRACT

Compounds having the formula

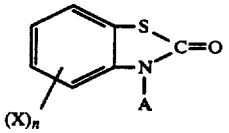

are found to be effective plant growth regulants.

8 Claims, No Drawings

AMIDES AND HYDRAZIDES OF 2-OXO-BENZOTHIAZOLINE-3-ACETIC ACID

Matter enclosed in heavy brackets [ ] appears in the original patent but forms no part of this reissue specification; matter printed in italics indicates the additions made by reissue.

This invention relates to the use of certain substituted benzothiazoline compounds as plant growth regulants. More specifically, this invention relates to the use of said compounds to regulate the growth of leguminous plants such as soybeans.

Many of the compounds described herein are novel. Therefore, this invention is directed further to said novel substituted benzothiazoline compounds.

In accordance with the novel aspects of the present invention, compounds having the following formula are effective plant growth regulants.

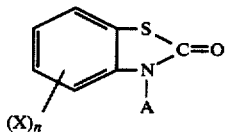

wherein A is selected from the group consisting of alkyl; (I)

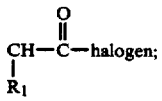
(II)

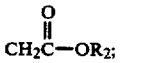
(III)

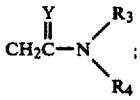
(IV)

and

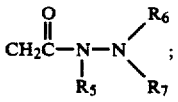
(V)

wherein $R_1$ is selected from the group consisting of hydrogen and lower alkyl; X is halogen; Y is selected from the group consisting of oxygen and sulfur; $R_2$ is selected from the group consisting of lower alkenyl, monohalo lower alkenyl, dihalo lower alkenyl, trihalo lower alkenyl, lower alkynyl, benzyl and substituted benzyl; $R_3$ is selected from the group consisting of hydrogen, lower alkenyl, lower alkynyl, pyridyl and pyridyl substituted by halogen; $R_4$ is selected from the group consisting of hydrogen and lower alkenyl; $R_5$ is selected from the group consisting of hydrogen and lower alkyl; $R_6$ and $R_7$ are independently selected from the group consisting of hydrogen, phenyl and lower alkyl; and n is 0 or 1; provided that $R_3$ and $R_4$ may be both hydrogen only when Y is sulfur; further provided that $R_6$ may not be hydrogen when $R_7$ is hydrogen.

Especially useful are those compounds having the following formula

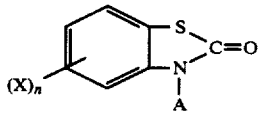

wherein A is selected from the group consisting of alkyl having up to ten carbon atoms; (I)

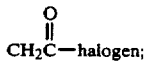
(II)

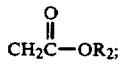
(III)

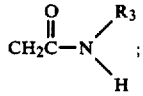
(IV)

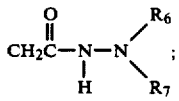
(V)

wherein $R_2$ is lower alkenyl, especially allyl or chlorinated allyl such as monochloroallyl, dichloroallyl and trichloroallyl; $R_3$ is selected from the group consisting of pyridyl and pyridyl substituted by halogen especially chloro; $R_6$ and $R_7$ are lower alkyl; X is halogen; and n is 0 or 1, but preferably 0.

As used herein, the term "lower alkyl", "lower alkenyl" and "lower alkynyl" is meant to include those alkyl, alkenyl and alkynyl groups having up to five carbon atoms inclusive.

The term "substituted benzyl" as used herein represents a radical having the structure

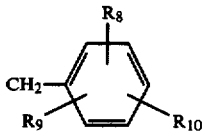

wherein $R_8$, $R_9$ and $R_{10}$ are independently selected from the group consisting of hydrogen, lower alkyl, trifluoromethyl and halogen. Preferred are those radicals in which $R_8$, $R_9$ and $R_{10}$ are on the 3, 4 and 5 positions of the ring.

As noted previously, many of the compounds described herein are believed to be novel. Said novel compounds are those having the structure as depicted above wherein A is selected from groups II, III, IV and V.

The compounds of the invention may be prepared in accordance with the procedures of the following examples.

EXAMPLE 1

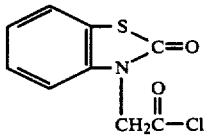

To a stirred slurry containing 41.9 grams (0.2 moles) of 2-oxo-3-benzothiazoline acetic acid and 100 ml. of benzene, 29.8 grams (0.25 moles) of thionyl chloride is added in one portion and then heated at reflux for three hours. After cooling to 0° C., stirring is continued at 0°-10° C. for 30 minutes. The solid is collected by filtration and air-dried at 25°-30° C. The acid chloride, mp. 122°-123° C., is obtained in 72% yield.

Anal. Calc'd. for $C_9H_6ClNO_2S$: C, 47:48; H, 2.66; Cl, 15.57; N, 6.15; S, 14.08. Found: C, 47.80; H, 2.70; Cl, 15.44; N, 6.19; S, 14.14.

EXAMPLE 2

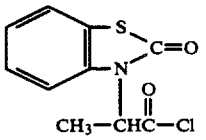

To a stirred slurry containing 44.7 grams (0.2 moles) of α-methyl-2-oxo-3-benzothiazoline acetic acid and 75 ml. of benzene, 29.8 grams (0.25 moles) of thionyl chloride is added in one portion and then heated at reflux for 3 hours. The solvent and excess thionyl chloride is removed in vacuo at a maximum temperature of 80°-90° C. at 1-2 mm. The acid chloride, a very viscous dark liquid, is obtained in 99% yield.

Anal. Calc'd. for $C_{10}H_8ClNO_2S$: N, 5.80. Found: N, 5.81.

EXAMPLES 3-5

To a stirred slurry containing 15.9 grams (0.07 moles) of the compound of Example 1 and 200 ml. of heptane, 0.2 mole of the appropriate aminopyridine is added in one portion. The stirred reaction mixture is heated at reflux for six hous and at 25°-30° C. for 18 hours. After the addition of 800 ml. of water, stirring is continued at 25°-30° C. for 30 minutes. The solid is collected by filtration, washed with water until the washings are neutral to litmus and air-dried at 25°-30° C. The data obtained are summarized in Table I.

TABLE I

| Example | Compound | Melting Point °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|
| 3 | N—(5-chloro-2-pyridyl)-2-oxo-3-benzothiazoline acetamide | 253-4[a] | 98 | 52.59 | 52.49 | 3.15 | 3.16 | 13.14 | 13.18 | | |
| 4 | N—(2-chloro-3-pyridyl)-2-oxo-3-benzothiazoline acetamide | 221-2[a] | 98 | 52.59 | 52.44 | 3.15 | 3.23 | 13.14 | 13.24 | | |
| 5 | N—(5-bromo-2-pyridyl)-2-oxo-3-benzothiazoline acetamide | 248-9[a] | 98 | 46.17 | 45.94 | 2.77 | 2.79 | 11.54 | 11.60 | 8.80 | 8.71 |

[a]Recrystallization from DMF.

EXAMPLE 6

To a stirred solution containing 15.1 grams (0.1 moles) of 2-benzothiazolol, 6.6 grams (0.1 moles) of 85% potassium hydroxide, 200 ml. of acetone and 10 ml. of water, 0.1 moles of 2-chloro-N,N-diallyl acetamide is added in one portion. The stirred reaction mixture is heated at reflux for six hours and at 25°-30° C. for 18 hours. After the addition of 800 ml. of water, stirring is continued for 30 minutes. The solid is collected by filtration, washed with water until the washings are neutral to litmus and air-dried at 25°-30° C. The data are summarized in Table II.

EXAMPLES 7-8

To a stirred slurry containing 22.8 grams (0.1 moles) of the compound of Example 1 and 200 ml. of heptane, 0.3 moles of the appropriate amine is added in one portion. The reaction mixture is stirred at 25°-30° C. for 2 days. After the addition of 800 ml. of water, stirring is continued at 25°-30° C. for 30 minutes. The solid is collected by filtration, washed with water until the washings are neutral to litmus and air-dried at 25°-30° C. The data obtained are summarized in Table II.

TABLE II

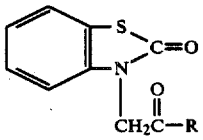

| Example | R | Melting Point °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|
| 6 | $-N(CH_2CH{=}CH_2)_2$ | 117-8[a] | 84 | 62.48 | 62.41 | 5.59 | 5.61 | 9.71 | 9.72 | 11.12 | 11.20 |
| 7 | $-N(CH_2C{\equiv}CH)_2$ | 149-50[b] | 77 | 63.36 | 63.28 | 4.25 | 4.25 | 9.85 | 9.84 | 11.28 | 11.18 |

TABLE II-continued

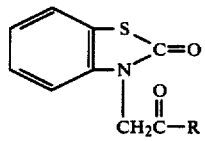

| Example | R | Melting Point °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|
| 8 | $-NCH(CH_3)_2$ \| $CH_2C{\equiv}CH$ | 137-8[a] | 52 | 62.48 | 62.24 | 5.59 | 5.65 | 9.71 | 9.63 | 11.12 | 11.05 |

[a]Recrystallization from isopropyl alcohol.
[b]Recrystallization from toluene.

EXAMPLES 9-10

To a stirred slurry containing 15.9 grams (0.07 moles) of the compound of Example 1 and 200 ml. of heptane, 0.2 moles of the appropriate hydrazine is added in one portion. The stirred reaction mixture is heated at reflux for six hours and 25°-30° C. for 18 hours. After the addition of 800 ml. of water, stirring is continued at 25°-30° C. for 30 minutes. The solid is collected by filtration, washed with water until the washings are neutral to litmus and air-dried at 25°-30° C. The data obtained are summarized in Table III.

TABLE III

| Example | Compound | Melting Point °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|
| 9 | 2',2'-dimethyl hydrazide of 2-oxo-3-benzo-thiazoline acetic acid | 204-5[a] | 63 | 52.57 | 52.33 | 5.21 | 5.21 | 16.72 | 16.64 | 12.76 | 12.82 |
| 10 | 2,-phenyl hydrazide of 2-oxo-3-benzo-thiazoline acetic acid | 222-3[b] | 73 | 60.18 | 60.27 | 4.38 | 4.39 | 14.04 | 13.98 | 10.71 | 10.81 |

[a]Recrystallization from isopropyl alcohol.
[b]Recrystallization from ethyl acetate.

To a stirred slurry containing 38 grams (0.2 moles) of 2-oxo-3-benzothiazoline acetonitrile, 15.2 grams (0.2 moles) of thiolacetic acid (dried over $MgSO_4$) and 300 ml. of anhydrous ethyl ether, dried hydrogen chloride gas is bubbled through the suspension at −5° to 0° C. for 3 hours. External cooling was removed and the reaction mixture is stirred at 25°-30° C. for 18 hours. The solid is collected by filtration, washed with 500 ml. of anhydrous ethyl ether and air-dried at 25°-30° C. for one hour. The solid (41 grams) was slurried with 700 ml. of water for one hour. After the addition of 300 ml. of water and 25 grams (0.25 moles) of concentrated hydrochloric acid stirring is continued at 25°-30° C. for another hour. The solid is collected by filtration, washed with water until neutral and air-dried at 25°-30° C. The product, 2-oxo-3-benzothiazoline ethanethioamide, mp. 205°-207° C. with decomposition, is obtained in 85% yield. After recrystallization from heptane/tetrahydrofuran (1:1), it melted at 216°-217° C.

Anal. Calc'd. for $C_9H_8N_2OS_2$; C, 48.19; H, 3.60; N, 12.49; S, 28.59. Found: C, 42.83; H, 3.60; N, 12.44; S, 28.49.

EXAMPLES 12-24

To a stirred solution containing 22.8 grams (0.1 moles) of compound 1 and 0.1 mole of the appropriate alcohol in 200 ml. of tetrahydrofuran, 11.3 grams (0.11 moles) of triethylamine is added in one portion. An exothermic reaction set in causing a temperature rise from 28° to about 60° C. The stirred mixture is heated at reflux for 24 hours. After cooling to 0° C., 800 grams of ice water is added and stirring continued at 0°-10° C. for one hour. The solid is collected by filtration, washed with water until neutral and air-dried at 25°-30° C. The data are summarized in Table IV.

TABLE IV

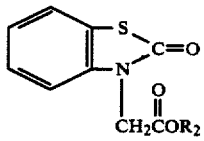

| Example | $R_2$ | Melting Point °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|
| 12 | $-CH_2CH{=}CH_2$ | 85-6[a] | 17 | 57.82 | 57.88 | 4.45 | 4.49 | 5.62 | 5.66 | 12.86 | 12.83 |
| 13 | $-CH_2CCl{=}CHCl$ | 97-8[a] | 67 | 45.30 | 45.50 | 2.85 | 2.89 | 4.40 | 4.47 | — | — |
| 14 | $-CH_2CCl{=}CCl_2$ | 101-2[a] | 65 | 40.87 | 40.92 | 2.29 | 2.38 | 3.97 | 4.01 | 9.09 | 9.12 |
| 15 | $-CH_2CCl{=}CH_2$ | 69-70[a] | 83 | 50.80 | 50.56 | 3.55 | 3.58 | 4.94 | 4.87 | 11.30 | 11.24 |

TABLE IV-continued

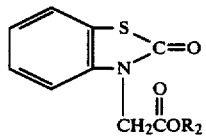

| Example | $R_2$ | Melting Point °C. | Percent Yield | Percent C Calc'd. | Percent C Found | Percent H Calc'd. | Percent H Found | Percent N Calc'd. | Percent N Found | Percent S Calc'd. | Percent S Found |
|---|---|---|---|---|---|---|---|---|---|---|---|
| 16 | $-CH_2CBr{=}CHBr$ | 95–6[b] | 52 | 35.41 | 35.59 | 2.23 | 2.26 | 3.44 | 3.46 | 7.88 | 7.93 |
| 17 | $-CH_2CH{=}CCl_2$ | 61–2[a] | 79 | 45.30 | 45.48 | 2.85 | 2.90 | 4.40 | 4.40 | 10.08 | 10.01 |
| 18 | $-CH_2C{\equiv}CH$ | 168–9[c] | 73 | 58.29 | 58.32 | 3.67 | 3.70 | 5.66 | 5.68 | 12.97 | 12.97 |
| 19 | 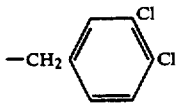 | 122–3[b] | 82 | 52.19 | 52.37 | 3.01 | 3.05 | 3.80 | 3.82 | 8.71 | 8.73 |
| 20 | 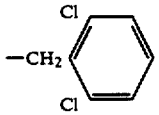 | 206–7[c] | 82 | 52.19 | 52.16 | 3.01 | 3.05 | 3.80 | 3.80 | 8.71 | 8.71 |
| 21 | $-CH_2CH{=}CHCl$ | 102–3[b] | 76 | 50.80 | 50.80 | 3.55 | 3.59 | 4.94 | 4.95 | 11.30 | 11.24 |
| 22 | $-CH_2C_6H_5$ | 101–2[a] | 72 | 64.20 | 64.12 | 4.38 | 4.41 | 4.68 | 10.71 | 10.64 | |
| 23 | 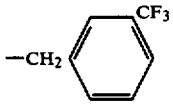 | 80–1[a] | 61 | 55.48 | 55.43 | 3.29 | 3.31 | 3.81 | 3.83 | 8.73 | 8.83 |
| 24 | 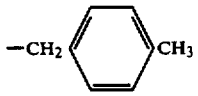 | 131–2[a] | 73 | 65.16 | 64.99 | 4.82 | 4.86 | 4.47 | 4.51 | 10.23 | 10.31 |

[a]Recrystallization from heptane/isopropyl alcohol.
[b]Recrystallization from isopropyl alcohol.
[c]Recrystallization from ethyl acetate.

EXAMPLES 25–30

To 30 ml. of ethyl alcohol, 2.3 grams (0.1 moles) of sodium is added and stirring continued until a solution resulted. To this stirred solution 15.1 grams (0.1 moles) of 2-benzothiazol and 0.1 mole of the appropriate alkyl bromide are added in one portion. The stirred reaction mixture is heated at reflux for two hours. The ethyl alcohol is removed in vacuo. The cooled residue is extracted with 200 ml. of ethyl ether and filtered to remove the salt. The ether is removed in vacuo. Compounds 29 and 30 are distilled. Compounds 27 and 28 are air-dried at 25°–30° C. The data are summarized in Table V.

TABLE V

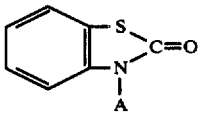

| Example | A | Melting Point °C. | Boiling Point °C. (mm.) | Percent Yield | Percent N Calc'd. | Percent N Found | Percent S Calc'd. | Percent S Found |
|---|---|---|---|---|---|---|---|---|
| 25 | $-CH_3$ | 75–6[a] | — | 98 | 8.48 | 8.54 | 19.41 | 19.4 |
| 26 | $-C_2H_5$ | — | 106–9/0.15[b] | 96 | 7.82 | 7.72 | 17.89 | 17.9 |
| 27 | $-C_3H_7$ | — | 122/0.30[c] | 73 | — | — | — | — |
| 28 | $-(CH_2)_8CH_3$ | — | 184/0.30 | 79 | — | — | — | — |
| 29 | $-(CH_2)_{11}CH_3$ | 38–42 | — | 87 | — | — | — | — |
| 30 | $-(CH_2)_{15}CH_3$ | 42–46 | — | 82 | — | — | — | — |

[a]Reported melting point 72° C.;
[b]Reported boiling point 152/4;
[c]Reported boiling point 148–153/3.

In accordance with the novel aspects of the present invention, the compounds are useful in regulating the growth of leguminous plants. As used herein, the regulation of "plant growth or development" is understood to mean the modification of the normal sequential development of a treated plant to agricultural maturity. Such modifications are most readily observed as changes in size, shape, color or texture of the treated plant or any of its parts. Similarly, changes in the quantities of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color is illustrative of higher chloryphyll activity indicative of improved rate of photosynthesis.

Although phytotoxic amounts of the active ingredient may be employed to exert a herbicidal effect, the regulation of plant growth in accordance with the present invention does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

By the term "active ingredient" is meant the active benzothiazoline compound of the above formula.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent or emulsifying agent or any suitable combination of these.

Illustrative finely divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray. Should the application of the plant growth composition to the plant growth medium be desired, this is accomplished by incorporating the composition in the soil or other media in the area where modification of the plants is desired.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.05 to about 10 or more pounds per acre. Preferred are foliar applications of from 0.05 to 5 pounds of the active ingredient per acre. In application to the soil habitat of germinant seeds, emerging seedlings and established vegetation for the regulation of plant growth, the active ingredients are applied in amounts of from 0.01 to 20 pounds per acre or more. The application to the soil of from 0.1 to about 10 pounds of active ingredient per acre is preferred. Foliar application to plants beginning to blossom are preferred over other types of applications.

Utilizing the benzothiazoline compounds of the present invention as the active ingredient in a plant growth regulating composition, several of said compounds were found to possess plant growth regulating activity when tested in accordance with the following procedure.

A number of soybean plants, variety Williams, are grown from seeds in plastic pots in the greenhouse for a period of one week at which time the plants are thinned to one plant per pot. When the second trifoliate leaf is fully expanded, the plants are treated with a solution of the active ingredient in acetone, water or N,N-dimethyl formamide. Aqueous Tween 20 is used as a surfactant.

When the fifth trifoliate leaf is fully expanded, the treated plants are compared with the non-treated control plants and the observations recorded.

Table VI, below, summarizes the results and observations made in accordance with the above procedure.

TABLE VI

| Compound of Example | Rate Kilos/Hectane | Response |
|---|---|---|
| 1 | 0.112 | Stature reduction, epinasty, inhibition of apical development. |
| | 0.56 | Stature reduction, epinasty, leaf alteration, inhibition of apical development, altered canopy. |
| | 2.80 | Stature reduction, epinasty, inhibition of apical development, leaf distortion. |
| 3 | 0.56 | Leaf alteration, altered canopy. |
| | 2.80 | Leaf distortion, leaf alteration, altered canopy. |
| 6 | 0.56 | Leaf alteration, altered canopy. |
| | 2.80 | Leaf distortion, altered canopy, axillary bud inhibition. |
| 9 | 0.112 | Stature reduction, leaf dis- |

TABLE VI-continued

| Compound of Example | Rate Kilos/Hectane | Response |
|---|---|---|
| | | tortion, leaf inhibition, altered canopy, inhibition of apical development. |
| | 0.56 | Stature reduction, leaf distortion, stem distortion, leaf inhibition, inhibition of apical development. |
| | 2.80 | Stature reduction, leaf distortion, epinasty, leaf inhibition, inhibition of apical development. |
| 11 | 0.112 | Leaf distortion, leaf alter ation, altered canopy. |
| | 0.50 | Leaf distortion, leaf inhibition, altered canopy, inhibition of apical development. |
| | 2.80 | Stature reduction, leaf distortion, leaf inhibition, altered canopy, inhibition of apical development. |
| 12 | 0.112 | Stature reduction, epinasty, leaf distortion, leaf inhibition, inhibition of apical development. |
| | 0.56 | Stature reduction, epinasty, leaf distortion, leaf inhibition, inhibition of apical development. |
| | 2.80 | Stature reduction, epinasty, leaf distortion, leaf inhibition, inhibition of apical development. |
| 13 | 0.112 | Stature reduction, stem distortion, leaf alteration, altered canopy, inhibition of apical development. |
| | 0.56 | Stature reduction, stem distortion, leaf alteration, altered canopy, inhibition of apical development. |
| | 2.80 | Stature reduction, epinasty, leaf distortion, altered canopy, inhibition of apical development. |
| 27 | 2.5 | Leaf distortion, leaf alteration, slight leaf burn, altered canopy. |
| 28 | 2.5 | Leaf alteration, altered canopy. |

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows:

[1. A compound having the formula

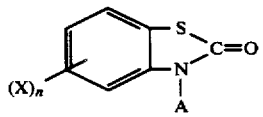

wherein A is selected from the group consisting of

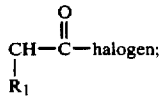

(I)

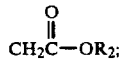

(II)

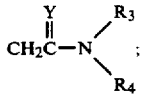

(III)

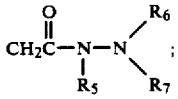

(IV)

wherein $R_1$ is selected from the group consisting of hydrogen and lower alkyl; X is halogen; Y is selected from the group consisting of oxygen and sulfur; $R_2$ is selected from the group consisting of lower alkenyl, monohalo lower alkenyl, dihalo lower alkenyl, trihalo lower alkenyl, lowe alkynyl, benzyl and benzyl optionally substituted by up to three substituents selected from the group consisting of lower alkyl, trifluoromethyl and halogen; $R_3$ is selected from the group consisting of hydrogen, lower alkenyl, lower alkynyl, pyridyl and pyridyl substituted by halogen; $R_4$ is selected from the group consisting of hydrogen and lower alkenyl; $R_5$ is selected from the group consisting of hydrogen and lower alkyl; $R_6$ and $R_7$ are independently selected from the group consisting of hydrogen, phenyl and lower alkyl; n is 0 or 1; provided that $R_3$ and $R_4$ may both be hydrogen only when Y is sulfur; further provided that $R_6$ may not be hydrogen when $R_7$ is hydrogen.]

[2. A compound according to claim 1 wherein A is

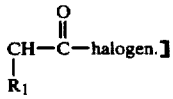

]

[3. A compound according to claim 2 wherein $R_1$ is hydrogen.]

[4. A compound according to claim 2 wherein said halogen is chlorine.]

[5. A compound according to claim 2 which is 2-oxo-3-benzothiazoline acetyl chloride.]

[6. A compound according to claim 1 wherein A is

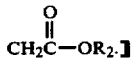

]

[7. A compound according to claim 6 wherein $R_2$ is lower alkynyl.]

[8. A compound according to claim 7 wherein $R_2$ is propynyl.]

[9. A compound according to claim 8 wherein n is 0.]

[10. A compound according to claim 6 wherein $R_2$ is lower alkenyl.]

[11. A compound according to claim 10 wherein said lower alkenyl is allyl, haloallyl, dihaloallyl or trihaloallyl.]

[12. A compound according to claim 1 wherein A is

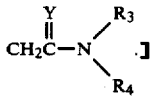

.]

[13. A compound according to claim 12 wherein Y is oxygen.]

[14. A compound according to claim 12 wherein $R_3$ is pyridyl or pyridyl substituted by halogen.]

[15. A compound according to claim 13 wherein $R_3$ is pyridyl or pyridyl substituted by halogen.]

[16. A compound according to claim 15 which is N-(5-chloro-2-pyridyl)-2-oxo-3-benzothiazoline acetamide.]

[17. A compound according to claim 12 which is 2-oxo-3-benzothiazoline ethane thioamide.]

[18. A compound according to claim 1 wherein A is

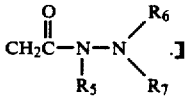

.]

[19. A compound according to claim 17 wherein $R_6$ and $R_7$ are lower alkyl.]

[20. A compound according to claim 18 wherein $R_6$ and $R_7$ are methyl.]

[21. A compound according to claim 19 wherein $R_5$ is hydrogen.]

[22. A compound according to claim 20 which is the 2',2'-dimethyl hydrazide of 2-oxo-3-benzothiazoline acetic acid.]

*23. A compound of the formula*

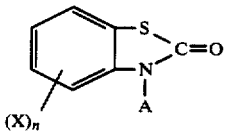

*wherein A is selected from the group consisting of*

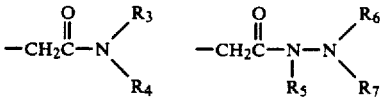

*wherein $R_3$ is selected from the group consisting of pyridyl and pyridyl substituted by halogen; $R_4$ is hydrogen; $R_5$ is selected from the group consisting of hydrogen and lower alkyl; $R_6$ and $R_7$ are independently selected from the group consisting of hydrogen, phenyl, and lower alkyl; n is 0 or 1; provided that $R_6$ may not be hydrogen when $R_7$ is hydrogen.*

*24. Compound of claim 23 wherein A is*

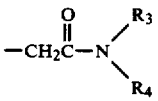

*25. Compound of claim 23 which is N-(5-chloro-2-pyridyl)-2-oxo-3-benzothiazoline acetamide.*

*26. Compound of claim 23 wherein A is*

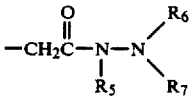

*27. Compound of claim 26 wherein $R_6$ and $R_7$ are lower alkyl.*

*28. Compound of claim 26 wherein $R_6$ and $R_7$ are methyl.*

*29. Compound of claim 26 wherein $R_5$ is hydrogen.*

*30. Compound of claim 26 which is 2',2'-dimethyl hydrazine of 2-oxo-3-benzothiazoline acetic acid.*

* * * * *